Figure 1:
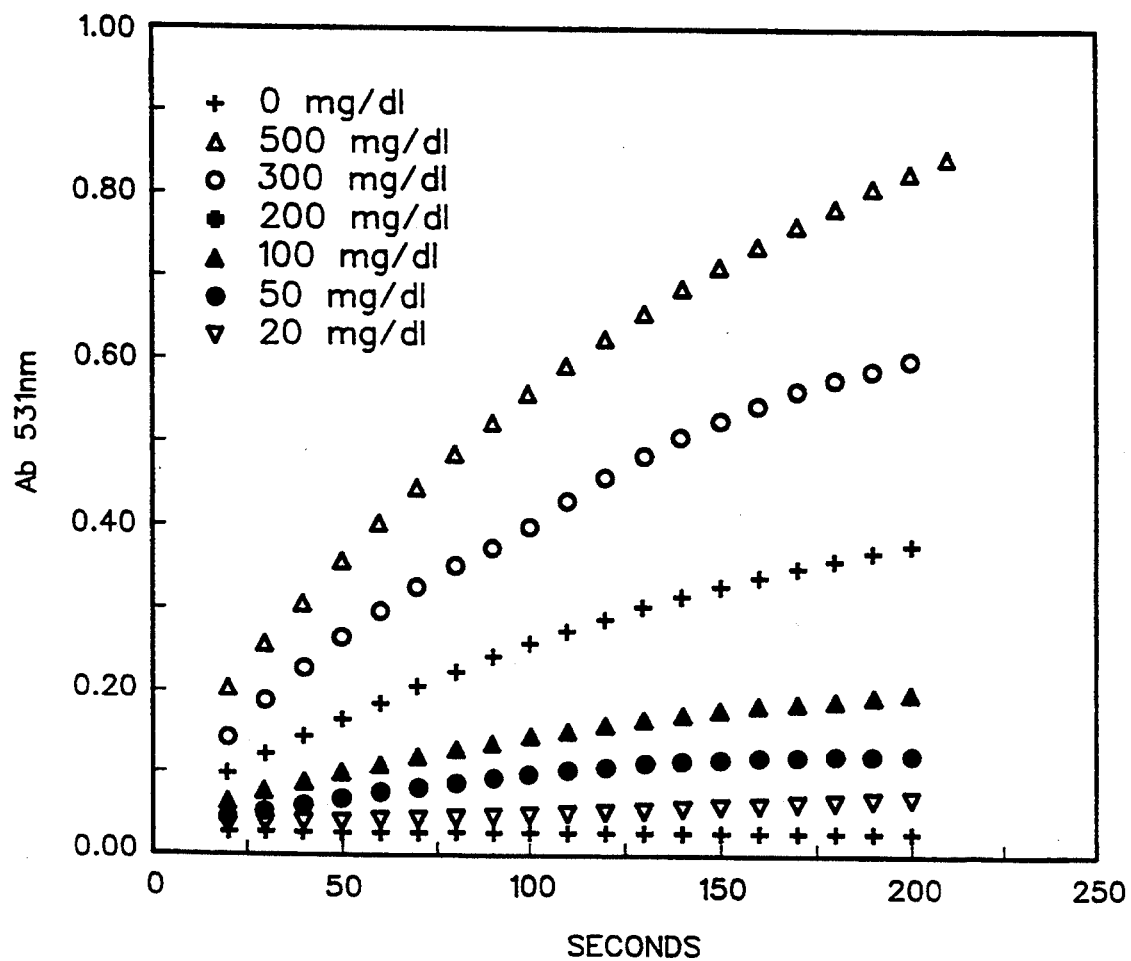

United States Patent [19]
Yip et al.

[11] Patent Number: 5,385,847
[45] Date of Patent: Jan. 31, 1995

[54] METHOD FOR THE DETERMINATION OF URINARY PROTEIN AND CREATININE

[75] Inventors: Kin F. Yip; Amy H. Chu; Brenda Tudor, all of Elkhart, Ind.

[73] Assignee: Miles Inc., Elkhart, Ind.

[21] Appl. No.: 160,239

[22] Filed: Dec. 2, 1993

[51] Int. Cl.$^6$ .............. G01N 33/546; G01N 33/53; G01N 33/557; G01N 33/00
[52] U.S. Cl. .................... 436/534; 435/7.1; 435/973; 436/98; 436/518
[58] Field of Search ............ 435/7.1, 973, 962; 436/98, 909, 534, 518

[56] References Cited

U.S. PATENT DOCUMENTS

| | | | |
|---|---|---|---|
| 2,785,057 | 3/1957 | Schwab et al. | 422/58 |
| 3,705,013 | 12/1972 | Dewhurst et al. | 436/98 |
| 4,205,954 | 6/1980 | Babson et al. | 436/534 |
| 4,990,075 | 2/1991 | Wogoman | 436/526 |

OTHER PUBLICATIONS

Watts, G. F., et al. Clinical Chemistry 32(8) 1544–47, 1988.
Fitzpatrick, M. M. et al. British Medical Journal 303:489–92, 1991.
Benedict, S. R. et al. J. Biol. Chemistry 114:515–532, 1936.
G. F. Watts et al. Practical Diabetes 9(3):84–86, 1992.

Primary Examiner—Esther M. Kepplinger
Assistant Examiner—Eve J. Wilson
Attorney, Agent, or Firm—Jerome L. Jeffers

[57] ABSTRACT

Disclosed is a method for the determination of urinary protein and creatinine in a single reaction vessel using a continuous process. The method involves adjusting the pH to a level suitable for carrying out an immuno assay for the protein and making such a determination by an immuno agglutination technique. Raising the pH to a level suitable for determining the creatinine quickly dissipates the cloudiness caused by the agglutination reaction, so that the creatinine determination can be carried out without delay.

7 Claims, 7 Drawing Sheets

METHOD FOR THE DETERMINATION OF URINARY PROTEIN AND CREATININE

BACKGROUND OF THE INVENTION

Human serum albumin (HSA), one of the proteins measurable in urine, has clinical significance for detecting the early stages of nephropathy, i.e. an abnormal state of the kidney. A high percentage of individuals suffering from insulin dependent diabetes mellitus (IDDM) and non-insulin dependent diabetes mellitus (NIDDM) eventually excrete HSA at levels above the upper end of the normal population. This stage of "microalbuminuria" becomes progressively worse and leads to nephropathy. Since the kidney damage at the stage of microalbuminuria can be controlled or reversed by administering appropriate therapy, it is well recognized that measuring microalbuminuria is part of the comprehensive care of IDDM and NIDDM.

Other urine born proteins, e.g. IgG, alpha-1-microglobulin, Bence-Jones protein and N-acetyl-b-D-glucosaminidase, are useful as markers to detect and differentiate prerenal, glomerular and postrenal forms of proteinuria. Proteinuria, which is indicated if the protein concentration in urine is greater than 30 mg/dL, is the common symptom for a variety of different kidney diseases. Accordingly, there is a need on the part of nephrologists, diabetologists and cardiologists for test methods that are sensitive, specific and quantitative for the determination of these proteins in urine.

In order to increase the sensitivity and specificity of urinary protein assays and minimize the problem of high urine flow rate resulting in urine dilution, protein/creatinine ratios are used in urine protein assay results to normalize the urine concentration. Typical urinary protein analyses involve immunoassays such as radioimmunoassay, enzyme immunoassay, latex assisted immunoassay and immunoturbidimetric assay. Common creatinine assays, such as the alkaline Jaffe and Benedict-Behre methods, are run at a high pH, typically in the range of from 11.5 to 12.5. The common practice in present day clinical laboratories is to run the protein and creatinine assays separately, and then combine the values obtained from these assays to generate the protein creatinine ratio. Since patients with high urine flow rates would have artificially low protein values because of the urine's dilution and since creatinine is a good marker for the dilution of urine, using the protein/creatinine ratio, therefore, eliminates the problem of urine dilution and gives a more accurate reflection of the true protein excretion rate.

In Clin. Chem. 32/8, 1544–1548 (1986); Watts et al discuss four immunochemical methods (radioimmunoassay, radial immunodiffusion, immunoturbidimetry and enzyme-linked linked immunosorbent assay) for measuring urinary albumin at low concentrations. They point out that diabetic nephropathy is a major cause of death in insulin dependent diabetics and that the clinical chemistry laboratory requires a technique that is sensitive, specific for albumin and practicable. Watts et al go on to point out in Practical Diabetes Vol. 9, No. 3, Pp. 84–86 that microalbuminuria is a supranormal quantity of urinary albumin which escapes detection Dy indicator dye binding tests and that it is a powerful marker of both early nephropathy and cardiovascular disease in patients with diabetes mellitus.

SUMMARY OF THE INVENTION

The present invention is a method for the determination of urinary protein and creatinine in a single reaction vessel using the same aliquot of urine sample. The method involves the steps of:

a) providing a urine sample suspected of containing protein and creatinine and, in either order;

b) adjusting the pH of the urine sample to a level suitable for carrying out an immunoassay for the protein concentration and then determining the protein concentration by an immunoassay technique; and c) adjusting the pH of the urine sample to a level suitable for carrying out an assay for creatinine and then determining the creatinine concentration in the urine sample.

After determination of the individual protein and creatinine concentrations, their ratio is calculated.

DESCRIPTION OF THE INVENTION

In practicing the present invention, it is possible to use either option A, in which creatinine is deter-mined before the protein or option B in which the protein concentration is initially determined followed by the determination of creatinine concentration in the urine sample being tested. Regardless of the order in which the determinations are carried out, it is necessary to adjust the pH of the urine sample to accommodate the requirements of the protein immunoassay which is carried out at a pH of about 7 to 9 which is the optimal pH range for this assay. The creatinine assay is carried out at a pH of from about 11.5 to 12.5 in order to deprotonate the creatinine so that the assay system can work properly. The first practical test for the determination of creatinine in urine, known as the Jaffe method, involves the formation of the red-yellowish brown colored creatinine picrate by the bonding of picric acid and creatinine in the alkaline solution. A more recent method for creatinine determination, known as the Benedict-Behre method, involves the reaction of another creatinine reactive reagent, 3,5-dinitrobenzoic acid, with creatinine in the alkaline medium. Any reagent which will provide a colored response when contacted with creatine at the high pH required to deprotonate it is suitable for use in this step.

The analytical method of the present invention can be carried out in either order of protein and creatinine determination. According to option A, a urine sample is mixed with a suitable reagent for creatinine determination and a strong alkali to generate color for the creatinine concentration measurement which is typically obtained by spectrophotometric means. The pH of the reaction mixture is then lowered using an appropriate acidifier and mixed with the antibody reagent to generate turbidity for the protein concentration measurement.

In option B, the urine sample is mixed with the antibody reagent to generate turbidity for the protein concentration measurement. An alkaline reagent and appropriate creatinine indicator are then added to raise the pH and to generate color for the creatinine concentration measurement.

While the volumes of urine sample and reagent solutions can be whatever is convenient for a particular analytical environment, rather small volumes, e.g. 1 to 50 $\mu$L of urine and 20 to 1,000 $\mu$L of buffer solution containing the creatinine reagent and the immuno reagent for the protein are sufficient.

When the determination is carried out using option A, a delay is encountered between the creatine and protein assay since the colored creatine reaction product will interfere with the turbidimetric determination assay for the protein in the next step. Accordingly, option B is the preferred method since it has been discovered that the agglutination products of the antibody/protein reaction dissolve almost immediately upon addition of the alkali and creatinine reagent, so that this part of the assay can be carried out within about 1 second of the protein determination. In this regard, a protein assay technique involving light scattering as in nephelometric or turbidometric assays involving immuno agglutination is particularly suitable for use in this invention. This can be an agglutination assay between antibodies and the protein or of the latex bound antibody agglutination type where an antibody, or fragment thereof, specific for particular epitopes of the protein, is bound to a water suspensible particle (e.g., polystyrene or other latex) and protein. By combining a large number of epitopic binding sites for the antibodies or antibody-latex and the plurality of epitopes on the protein, a large aggregate can be formed between the antibodies or antibody-latex and the protein. This aggregate creates the turbidity which can be measured spectrophotometrically and the degree of turbidity correlated to the concentration of protein in the test sample. The following example illustrates an analysis for HSA and creatinine employing the method of the present invention.

EXAMPLE 1

Measuring HSA and Creatinine by Option A

Figure 2:
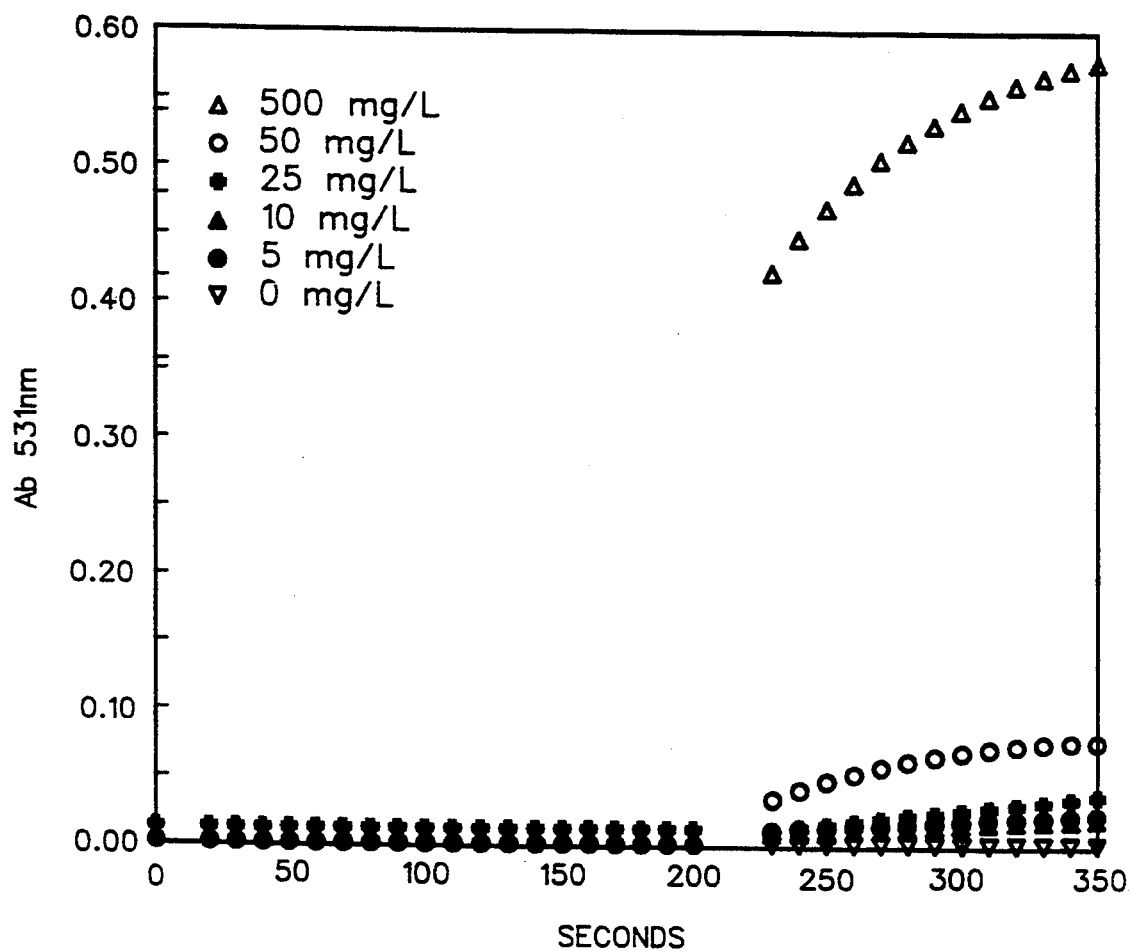

To a 1.08 mL of a 5% polyethylene glycol solution was added 60 μL of a sample consisting of HSA, creatinine or a mixture of HSA and creatinine. This was followed by 30 μL of alkaline reagent (potassium phosphate, pH 13.5) and 30 μL of DNBA to initiate the creatine assay whereupon the absorption at 531 nm was measured for 200 seconds. The rate of increase of the absorption is proportional to the concentration of the creatinine in the sample and is illustrated by FIG. 1. From FIG. 1 it can be determined that the concentration of creatinine in a sample can be measured accurately between a range of 20 to 500 mg/dL. Right after the measurement, 50 μL of Tris HCl (Tris buffer is tris (hydroxymethylaminomethane)) was added. After the colored creatine reaction product was destroyed by the buffer (a few minutes), 60 μL of antiserum (goat antibody for HSA) was added. The absorption at 531 nm was again measured for 150 seconds. The rate of increase of the absorption is proportional to the concentration of HSA in the sample as illustrated by FIG. 2. From FIG. 2 it can be determined that the concentration of HSA can be measured accurately within the range of 5 to 500 mg/L.

Measuring HSA and Creatinine by Option B

Figure 3:
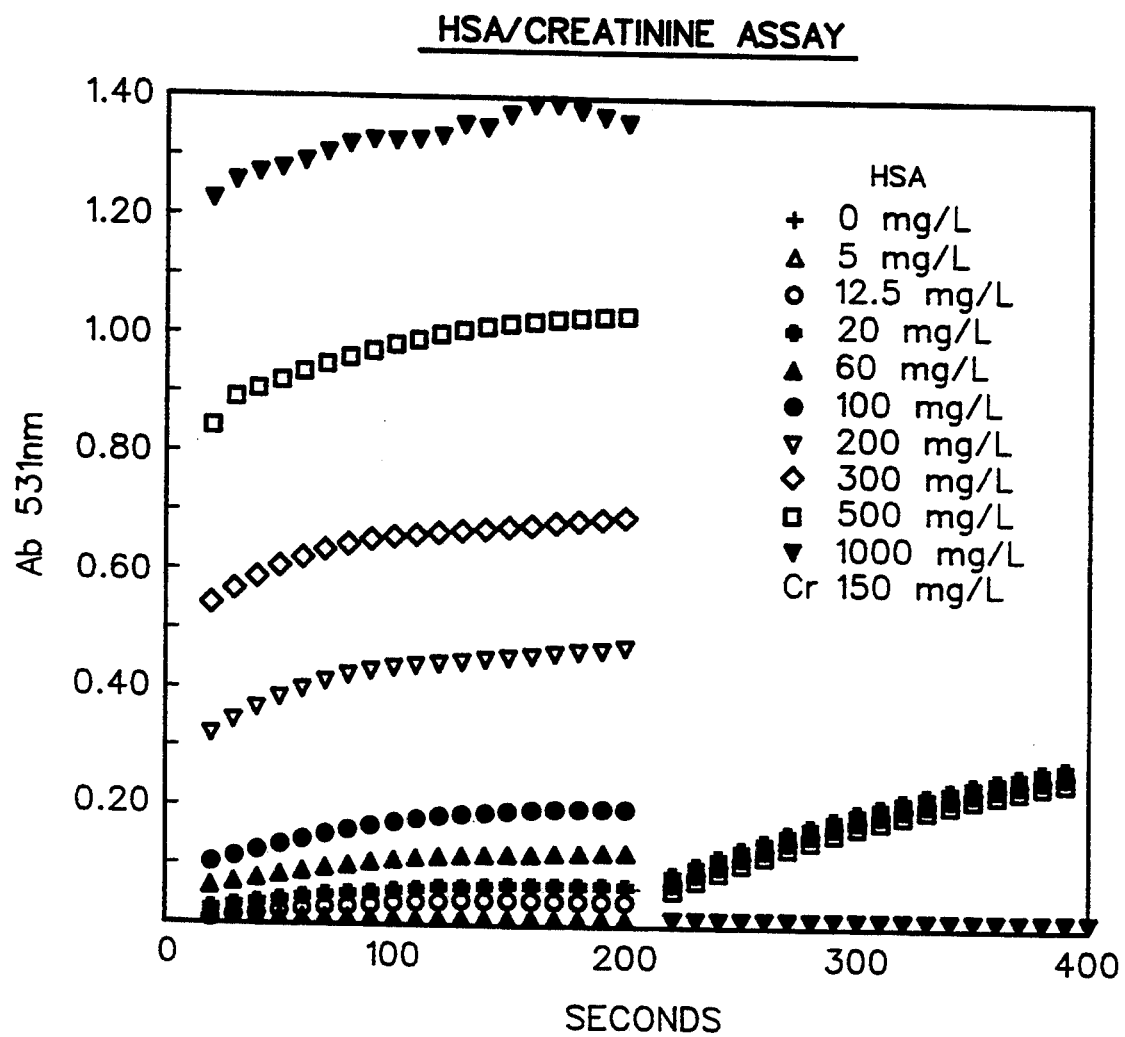

To a 1.08 mL sample of assay buffer (pH 8.5) consisting of 4% polyethylene glycol, 10 mM Tris, 10 mM EDTA and 0.02% sodium azide was added 60 μL of sample (HSA, creatinine or a mixture of HSA and creatinine). This was followed by 60 μL of antiserum reagent to initiate the HSA assay. The absorption at 531 nm was measured for 200 seconds. The rate of increase in the absorption is proportional to the concentration of HSA in the sample. After the turbidometric HSA measurement, 30 μL of the alkaline reagent was added followed by 30 μL of 3,5-dinitrobenzoic acid (DNBA) reagent. The turbidity cleared immediately after addition of the alkali so that no delay was encountered in commencing the creatinine assay. The absorption at 531 nm was again measured for three minutes. The rate of increase in absorption is proportional to the concentration of the creatinine in the sample. The combined HSA and creatinine assays are illustrated by FIG. 3. From FIG. 3 it can be determined that the concentration of HSA in a sample can be measured accurately between a range of 5 to 1,000 mg/L and subsequently the creatinine (150 mg/dL) in the samples can be accurately measured.

While the combined analysis of protein and creatinine in urine works well in the above-described wet analysis format, we have found that it is particularly suitable for adaptation to a reaction vessel for performing sequential analytical assays such as that disclosed in U.S. Pat. No. 4,990,075. This patent discloses a reaction vessel having a substantially horizontal axis of rotation and an analytical reagent reaction channel containing first and second reaction zones incorporated with first and second analytical reagents which interact with an analyte in a liquid test sample to produce a detectable response as a function of the analyte. The second reaction zone is situated a predetermined distance away from and in fluid communication with the first reaction zone whereby a liquid test sample disposed in the reaction channel is capable of being transported by gravity along the reaction channel between the reaction zones by rotating the reaction vessel about the axis of rotation. The reaction vessel has liquid test sample delivery means for providing a unidirectional flow of the liquid test sample into the reaction vessel and inlet means in liquid communication with the delivery. means for introducing the liquid test sample into the delivery means.

Figure 4:
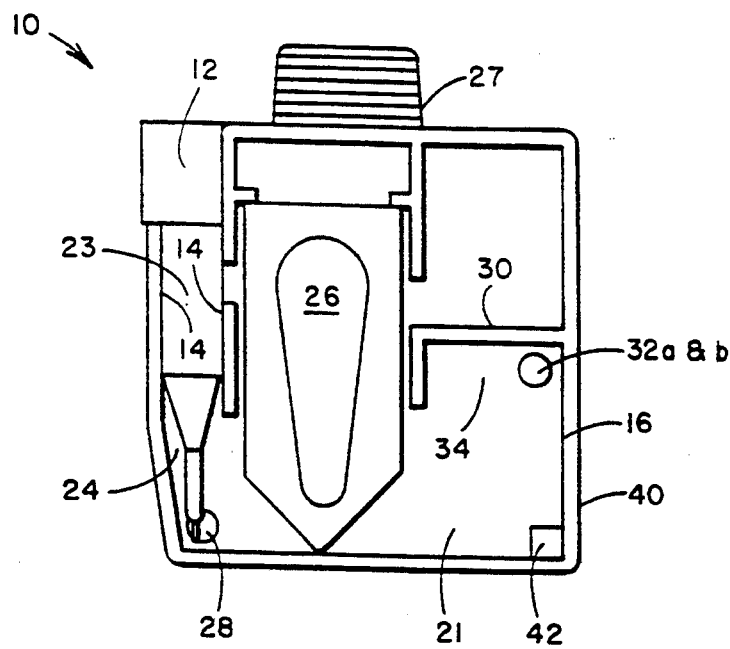
Figure 5:
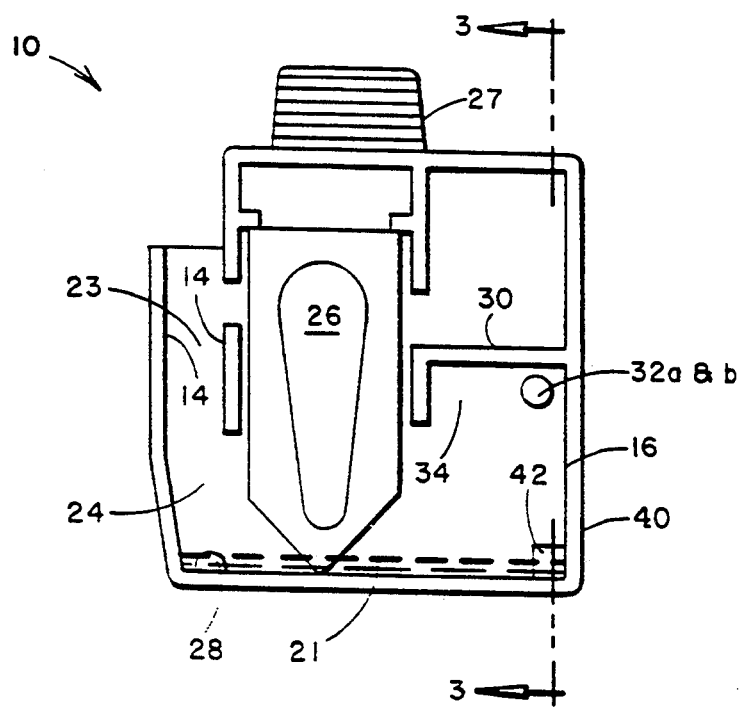

The protein/creatinine assay can be carried out in this reaction vessel using either configuration A or B described hereafter. Referring to FIG. 4, using configuration A, a mixture of the antibody and an additive such as a monosaccharide, disaccharide or oligosaccharide is dried onto the first reagent site 28 in the first reaction chamber 24 of the reaction vessel 10. The additive is desirable since it tends to stabilize the antibody during drying and during its long term storage after having been dried. The additives also provide physical stability to prevent peeling and cracking of the dried reagent. The device has an outer wall 40. The device has inner walls 14 which form a delivery chamber 23 permitting the introduction of a liquid test sample, such as a small amount of urine to be analyzed, into the device, and, since the delivery chamber is in fluid communication with reaction channel 21, the liquid test sample can enter the reaction channel through the delivery chamber and be caused to flow along the reaction channel by clockwise rotation of the device along its horizontal axis of rotation. The test sample is conveniently delivered through capillary dispenser 12 as depicted in FIG. 4. Since only a small amount of urine will be introduced through the delivery channel, additional reaction fluid containing suitable buffers can be introduced either through the delivery channel or from another source such as liquid delivery reservoir 26 adapted to contain a buffer and/or liquid reagent for performing the analytical assay procedures of the present invention. The liquid delivery reservoir comprises a reservoir body 27 having a depression therein 26 to act as fluid reservoir for holding the fluid until needed which is covered by a membrane (not shown) which can be removed to allow the fluid in the reservoir 26 to flow into reaction channel 21 as is depicted in FIG. 5. Simple manipulation of the device will cause the liquid test sample carried by the fluid from liquid reservoir 26 to flow into position for viewing through viewing chamber 42.

Figure 6:
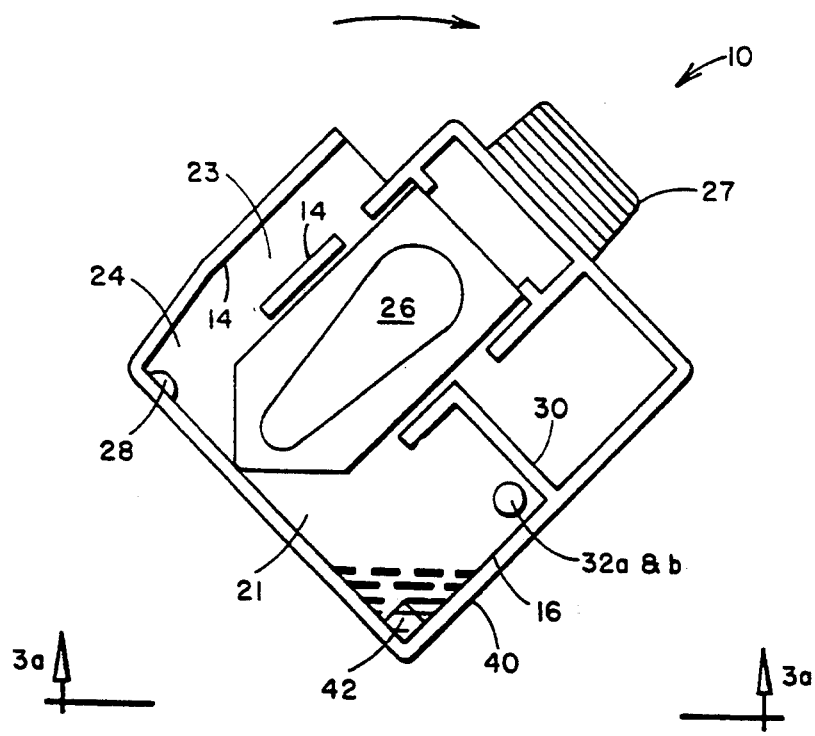
Figure 8:
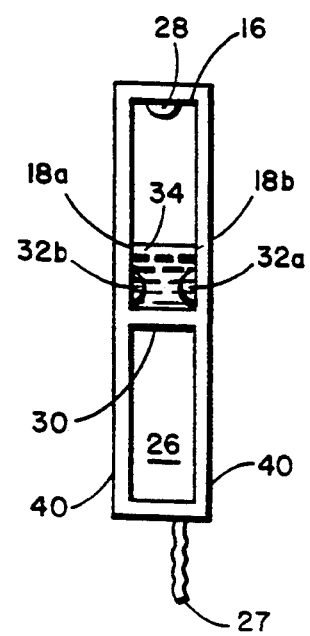

The reaction vessel has a first reaction zone 24, which is typically disposed in the reaction channel 21. The first reaction zone contains dried antibody reagent at the first reagent site 28 which is typically attached to one of the side walls depicted as 18 a & b in FIG. 8 or to the inner wall of the reaction vessel 16. Suitable rotation of the device will bring the reaction fluid into contact with the dried antibody reagent at site 28 to facilitate its dissolution. When the antibody reagent is adequately dissolved in the reaction fluid carrying the urine test sample, the device 10 is rotated 45° to the right to cause the fluid to cover viewing port 42, as depicted in FIG. 6, where spectrophotometric readings are taken and the change in turbidity as a function of time is determined. By comparing these readings with graphs prepared using a urine sample containing known amounts of protein, the protein concentration in the test sample is determined.

The system is now ready for the second step of the analytical procedure which is the determination of creatinine concentration. A mixture of a suitable creatinine reagent such as DNBA and a similar additive and a water soluble polymer such as a non-reactive protein, polyethylene glycol, polyether or polyvinylalcohol to serve the same function as the sugar additive, is dried onto the second reagent site 32a located in the second reaction zone 34 formed by inner walls 30. A mixture of alkaline reagent and additive together with a water soluble polymer is dried onto the third reagent site 32b which is on the opposite wall of the vessel from reagent site 32a so that they are physically separated from each other. A liquid buffer reagent typically comprising polyethylene glycol to enhance the agglutination, Tris, EDTA and sodium azide as preservatives, potassium chloride as a stabilizer for the antibody and to prevent the formation of undesirable reaction products and a non-reactive protein such as gelatin, hydrolyzed gelatin, ovalbumin and casein to prevent non-specific absorption of proteins to the reaction vessel at a pH between 7 and 9 is introduced into the vessel along with the urine sample containing the protein to be assayed and creatinine.

Figure 7:
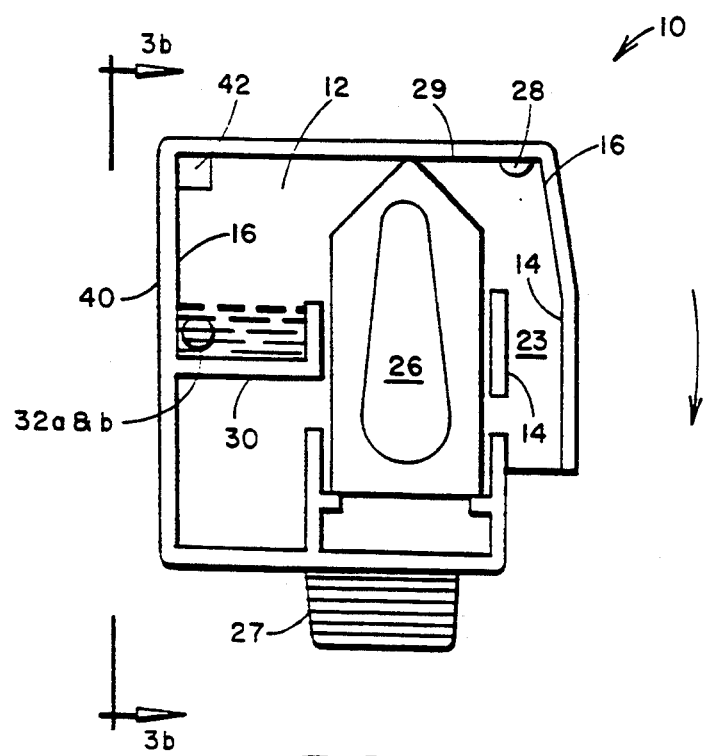

After the protein assay is completed, the vessel is rotated another 135° to the right to invert it from its original position and bring the buffer solution into contact with the dried creatinine detecting reagent at reagent site 32a and the alkaline reagent at site 32b thereby causing their solubilization as depicted in FIG. 7. This results in an increase in the buffer solution's pH to the level of 11.5 to 12.5 necessary for the creatinine determination reaction to take place. Unexpectedly, the creatinine concentration can be spectrophotometrically determined shortly after this solubilization step, i.e. within 1 second or more typically within the time that is required to mix the sample and start the measurement (about 5 seconds) due to the discovery that the cloudiness of the buffer solution caused by the protein/antibody agglutination clears rapidly when the solution is contacted with the creatinine determination agent and the strong alkali This speeds up the assay system considerably since the cloudy buffer solution would normally take days to become sufficiently clear for the colorimetric creatinine analysis to be successfully carried out. Typically, an operator in a busy clinical laboratory would wait no more than about 30 minutes and preferably no more than 5 or even 1 minute after completing the protein assay before initiating the assay for creatinine. If desired the creatinine assay can be carried out immediately after taking the spectrophotometric measurement of the protein. After dissolution of the creatinine detecting reagent and alkaline reagent the device is rotated back to the position depicted in FIG. 6 where spectrophotometric readings are taken through viewing port 42 over a period of time to obtain color formation as a function of time which can be compared with creatinine determinations made on sample having known concentrations of creatinine to ascertain the unknown creatine concentrations.

Turning to configuration B, a mixture of antibody and additive is dried onto the first reagent site 28 and the mixture of alkaline reagent and additive is dried onto the second reagent site, either 32a or b. The liquid buffer agent comprising the creatinine reagent, polyethylene glycol, Tris, EDTA, sodium azide, potassium chloride and a non-reactive protein at a pH of 7 to 9 is introduced to the reaction vessel along with a urine sample containing the protein and creatinine. The buffer solution solubilizes the antibody reagent as before and the protein concentration is determined spectrophotometrically through viewing port 42. After determination of the protein concentration the buffer solution is brought into contact with the dried alkaline reagent at the second reagent site to thereby solubilize the alkali and raise the pH to the level necessary for the creatinine assay to be carried out. Either configuration can be used in conjunction with the previously described reaction vessel to achieve equivalent results.

In a particular embodiment, goat antiserum against HSA was used as the antibody reagent by drying it onto the first reagent site. This material is commercially available and can be used without further treatment. Preferably, the antiserum is concentrated two-fold and combined with a sucrose/trehalose mixture at a level of from 2–5% as stabilizer. A 15 λL sample of the reagent is dried onto the reaction site using a drying tunnel operated at 60° C. and a drying time of 15 minutes.

The alkaline reagent for creatinine comprises either an alkali hydroxide solution (e.g. 2.5 M KOH) or a mixture of alkaline buffering materials such as phosphate, borate or guanidine derivatives to maintain the proper pH and the alkali hydroxide. Typically, 15 $\mu$L of a mixture of 1M phosphate and 4M potassium hydroxide combined with the sucrose/trehalose mixture is dried onto the second reagent site using a drying tunnel operated at 60° C. with a drying time of 15 minutes.

The preferred creatinine reagent, DNBA, is typically applied to the second reagent site from its 1.4M aqueous solution containing 10% of either the sugar or polymer additive by applying a 15 $\mu$L sample of the solution and drying as before.

In operation, using configuration A, a 0.57 mL sample of the buffer solution (4% polyethylene glycol, 25 mM Tris, 5 mM EDTA, 0.1% sodium azide and 0.1% gelatin as the non-reactive protein; pH=8.5) and 30 $\mu$L of sample (HSA and creatinine in urine) was introduced into the cartridge to initiate the reaction. After measurement of the sample blank, the antibody reagent was dissolved and the absorption at 531 nm was measured for 120 seconds. The rate of increase in absorption was used to determine the HSA concentration. The alkaline reagent and DNBA reagent were then dissolved and the creatinine concentration determined by the rate of increase in absorption. It was possible to carry out this step within as little as 1, usually 1-5, seconds of the HSA determination since the solution cleared rapidly after the dissolution of the creatinine reagents.

An analysis employing configuration B was carried out in which 0.57 mL of a solution of DNBA in buffer (4% polyethylene glycol, 25 mM Tris, 5 mM EDTA, 0.1% sodium azide, 100 mM KCl and 10 mg/mL DNBA); pH 8.5 and 30 µL of HSA and creatinine in urine was introduced into the cartridge to initiate the reaction. After measurement of the sample blank, the antibody reagent was dissolved and the absorption at 531 nm was measured for one to two minutes. The HSA concentration was determined as a function of the rate of increase in absorption. The alkali reagent was then dissolved and the absorption at 531 nm was again measured for three minutes with the creatinine concentration being determined from the rate of increase in absorption.

Figure 9:
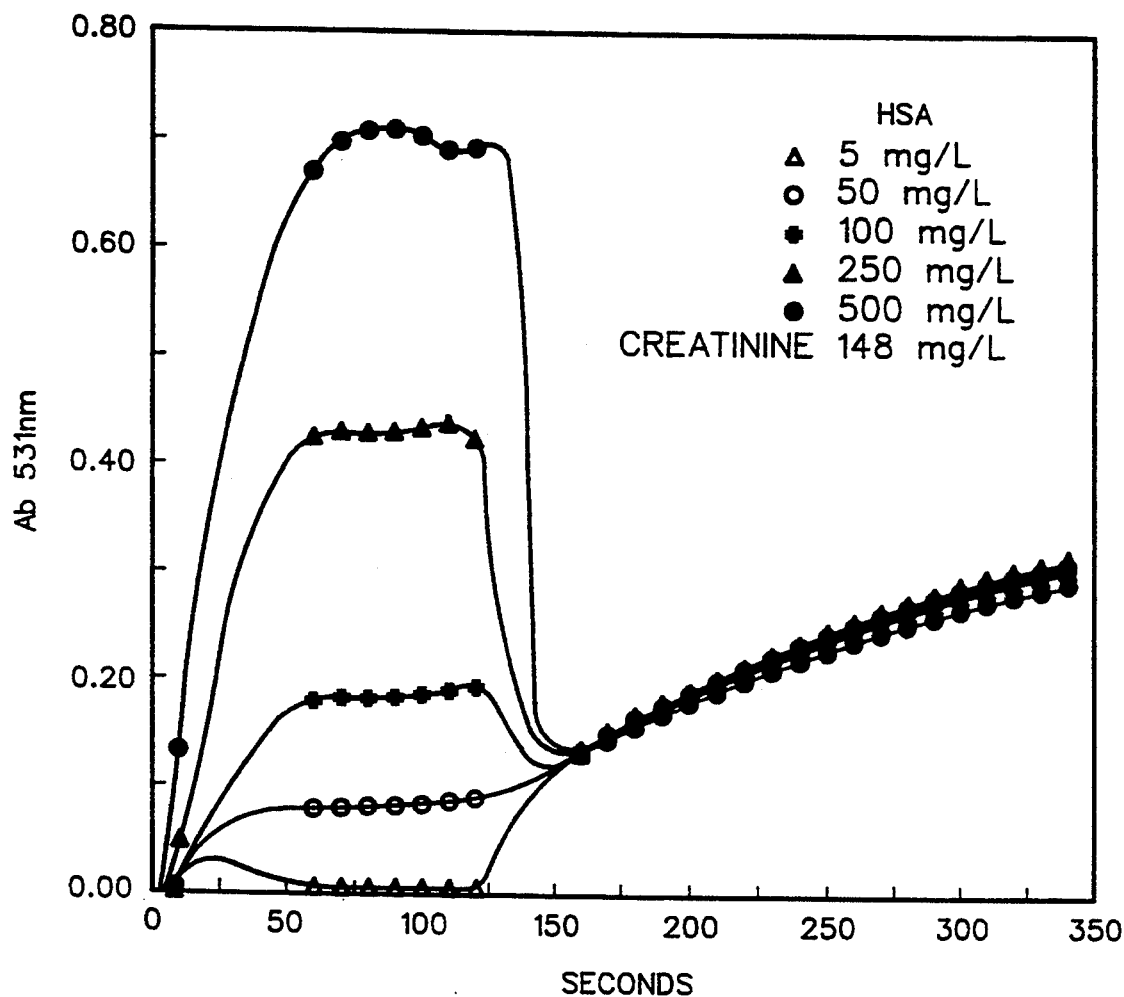

FIG. 9 illustrates the reaction response profile of samples containing different concentrations of HSA and 148 mg/dL creatinine measured by this procedure. From FIG. 9 it can be determined that the concentration of HSA in a urine sample can be accurately measured between a range of 5 to 500 mg/L and subsequently the creatinine (148 mg/dL) in the sample can be measured accurately.

What is claimed is:

1. A method for the determination of a protein and creatinine in a urine sample which method comprises the steps of:
   a) providing a urine sample containing the protein and creatinine; and:
   b) first adjusting the pH of the urine sample to form an admixture of from about 7 to 9, adding an antibody which specifically binds the protein to form a second admixture, and then determining the protein concentration in the second admixture by immunoagglutination; and next
   c) adding an alkaline reagent to the second admixture to form a third admixture having a pH of from about 11.5 to 12.5 and then determining the creatinine concentration in the third admixture by the addition of an indicator reagent for the colorimetric determination of creatinine and measuring the color change caused by the interaction of the creatinine and the indicator reagent within about 30 minutes of the addition of the indicator reagent to determine the creatinine concentration.

2. The method of claim 1 wherein the indicator reagent for the colorimetric determination of creatinine is picric acid or 3,5-dinitrobenzoic acid.

3. The method of claim 1 wherein an antibody specific for the protein under consideration is bound to a water suspensible particle.

4. The method of claim 1 wherein the creatinine test is initiated within about 1 to 5 seconds from the time the pH is raised.

5. A method for the determination of a urinary protein and creatinine in a urine sample using a single reaction vessel which comprises the steps of:
   a) providing the urine sample containing the urinary protein and creatinine;
   b) adjusting the pH of the urine sample to form an admixture having a pH of from about 7 to 9 adding an antibody which specifically binds to the protein to form a second admixture and determining the protein concentration in the second admixture by immunoagglutination;
   c) adding an alkaline reagent to the second admixture to form a third admixture having a pH of from about 11.5 to 12.5; and
   d) determining the concentration of creatinine in the third admixture by the addition of an indicator reagent for the colorimetric determination of creatinine and measuring the color change caused by the interaction of the creatinine and reagent within about 30 minutes of the addition of the the indicator reagent to determine the creatinine concentration.

6. A method for the determination of a urinary protein and creatinine in a urine sample using a single reaction vessel which comprises the steps of:
   a) providing a reaction vessel having a substantially horizontal axis of rotation and an analytical reagent reaction channel containing first and second reaction zones said first reaction zone incorporated with a dry antibody specific for the urinary protein and said second reaction zone incorporated with a dry indicator reagent for the colorimetric determination of creatinine and a dry basic reagent which raises the pH of a reaction fluid introduced into the reaction channel to a level of from about 11.5 to 12.5;
   b) introducing a urine sample suspected of containing urinary protein and creatinine and buffered diluent fluid to provide an admixture at a pH of from about 7 to 9 into the reaction vessel and bringing it into contact with the dried antibody to thereby dissolve the antibody to form a second admixture and cause an increase in the turbidity of the second admixture by interaction of the antibody and the urinary protein;
   c) determining the concentration of the urinary protein based on the change in turbidity as a function of time;
   d) bringing the second admixture and the indicator reagent for the colorimetric determination of creatinine into contact with the dry basic reagent in the second reaction zone to thereby dissolve this basic reagent to form a third admixture and raise the pH of the third admixture to a level of from about 11.5 to 12.5; and
   e) determining the concentration of creatinine by spectrophotometric photometric means within about 30 minutes of the addition of the indicator reagent to thereby determine the creatinine concentration.

7. The method of claim 6 wherein the determination of creatinine is initiated within 1-5 seconds.

* * * * *